(12) United States Patent
Jin et al.

(10) Patent No.: US 12,123,825 B2
(45) Date of Patent: Oct. 22, 2024

(54) SYNCHRONOUS DETECTION SYSTEM AND DETECTION METHOD FOR TRACE NITROGEN-OXYGEN COMPOUND BASED ON PHOTOACOUSTIC SPECTROMETRY

(71) Applicant: Anhui University of Science and Technology, Huainan (CN)

(72) Inventors: Huawei Jin, Huainan (CN); Xu Wang, Huainan (CN); Haowei Wang, Huainan (CN)

(73) Assignee: Anhui University of Science and Technology, Huainan (CN)

( * ) Notice: Subject to any disclaimer, the term of this patent is extended or adjusted under 35 U.S.C. 154(b) by 0 days.

(21) Appl. No.: 18/432,313

(22) Filed: Feb. 5, 2024

(65) Prior Publication Data

US 2024/0175803 A1 May 30, 2024

Related U.S. Application Data

(63) Continuation of application No. PCT/CN2022/087118, filed on Apr. 15, 2022.

(30) Foreign Application Priority Data

Mar. 29, 2022 (CN) .......................... 202210324523.6

(51) Int. Cl.
  *G01N 21/17* (2006.01)
  *G01N 1/14* (2006.01)
  *G01N 33/00* (2006.01)

(52) U.S. Cl.
  CPC ........... *G01N 21/1702* (2013.01); *G01N 1/14* (2013.01); *G01N 33/0027* (2013.01);
  (Continued)

(58) Field of Classification Search
  CPC .. G01N 21/1702; G01N 1/14; G01N 33/0027; G01N 2021/1704; G01N 2201/06113; G01N 2201/0636
  (Continued)

(56) References Cited

U.S. PATENT DOCUMENTS

2009/0128819 A1* 5/2009 Van Kesteren ........ A61B 5/411
  356/437
2012/0271188 A1* 10/2012 Van Kesteren .......... G01H 5/00
  600/532
(Continued)

FOREIGN PATENT DOCUMENTS

CN 101163956 A 4/2008
CN 202404020 U 8/2012
(Continued)

OTHER PUBLICATIONS

Grant Notification issued in counterpart Chinese Patent Application No. 202210324523.6, dated Oct. 20, 2022.
(Continued)

*Primary Examiner* — Marrit Eyassu
(74) *Attorney, Agent, or Firm* — Westbridge IP LLC

(57) ABSTRACT

Disclosed is a synchronous detection system for a trace nitrogen-oxygen compound based on photoacoustic spectrometry, including a NOx (Nitrogen Oxide) detection air channel, a dust detection air channel and a double-photoacoustic spectrometry detection mechanism which are mutually connected in parallel; the NOx detection air channel includes a background interference detection air pipe, a $NO_2$ detection air pipe and a NO detection air pipe that are mutually connected in parallel, and a NOx photoacoustic detection cavity; and the dust detection air channel includes a dust detection air pipe and a dust photoacoustic detection cavity communicating with the dust detection air pipe.

5 Claims, 1 Drawing Sheet

(52) U.S. Cl.
CPC ............... *G01N 2021/1704* (2013.01); *G01N 2201/06113* (2013.01); *G01N 2201/0636* (2013.01)

(58) Field of Classification Search
USPC ........................................................ 73/24.02
See application file for complete search history.

(56) References Cited

U.S. PATENT DOCUMENTS

| | | | | |
|---|---|---|---|---|
| 2015/0112221 A1* | 4/2015 | Von Sicard | ............ | A61B 5/097 600/532 |
| 2021/0018430 A1 | 1/2021 | Gong et al. | | |

FOREIGN PATENT DOCUMENTS

| | | | | |
|---|---|---|---|---|
| CN | 104237154 A | 12/2014 | | |
| CN | 110441241 A | 11/2019 | | |
| CN | 112147076 A | 12/2020 | | |
| CN | 112730185 A | 4/2021 | | |
| CN | 215574610 U | 1/2022 | | |
| DE | 102007014519 A1 | 10/2008 | | |
| WO | WO-2006114766 A2 * | 11/2006 | ............ | A61B 5/083 |

OTHER PUBLICATIONS

Xu et al., Gas measurement system of NO and NO2 based on photoacoustic spectroscopy, Acta Phys. Sin., 2013, 62 (20), pp. 121-127, dated Oct. 23, 2013.

* cited by examiner

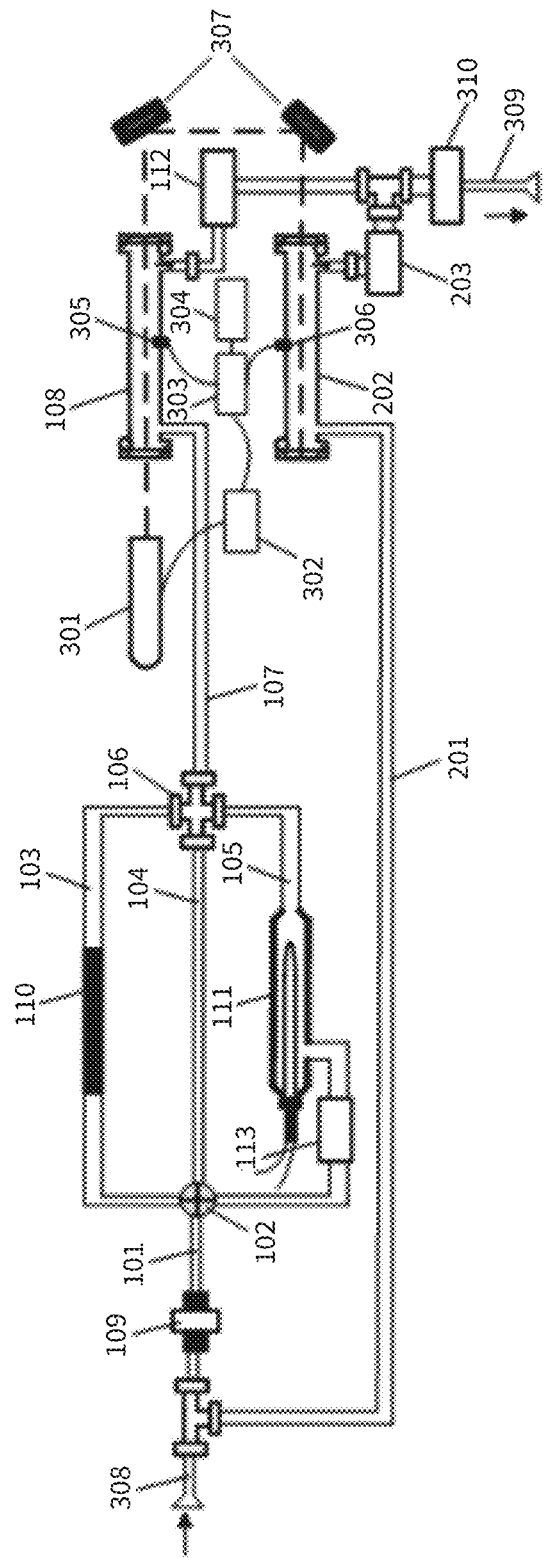

SYNCHRONOUS DETECTION SYSTEM AND DETECTION METHOD FOR TRACE NITROGEN-OXYGEN COMPOUND BASED ON PHOTOACOUSTIC SPECTROMETRY

CROSS-REFERENCE TO RELATED APPLICATIONS

This application is a continuation of International Application No. PCT/CN2022/087118, filed on Apr. 15, 2022, which claims priority to Chinese Patent Application No. 202210324523.6, filed on Mar. 29, 2022. The disclosures of the above-mentioned applications are hereby incorporated by reference in their entireties.

TECHNICAL FIELD

The present disclosure relates to the technical field of gas detection, and in particular to a synchronous detection system and a detection method for a trace nitrogen-oxygen compound based on photoacoustic spectrometry.

BACKGROUND

With the development of society and economy, environmental pollution has seriously threatened people's physical and mental health, so it is extremely urgent to master pollution mechanisms in real time. As main emission products of a fossil fuel, artificial combustion, natural lightning and a microorganism, NOx (Nitrogen Oxide) plays an important role therein, not only disturbs atmospheric oxidation, but also is the main source for serious pollution such as photochemical smoke, a respiratory disease and acid rain.

NOx in the atmosphere is common in NO and $NO_2$, with a content of ppb magnitude and belonging to trace gas, and when detecting the content thereof, three puzzles exist: 1) the trace gas has a great detection difficulty, 2) the detection synchronization for NO and $NO_2$ is not high, and 3) greatly affected by dust, but the synchronous detection for the dust cannot be achieved.

SUMMARY

The main purpose of the present disclosure is to provide a synchronous detection system and a detection method for a trace nitrogen-oxygen compound based on photoacoustic spectrometry, aiming at solving the technical issue that the detection synchronization for NO and $NO_2$ is not high and the synchronous detection for dust cannot be achieved in the existing technology.

To achieve the foregoing purpose, the present disclosure provides a synchronous detection system for a trace nitrogen-oxygen compound based on photoacoustic spectrometry, including a NOx detection air channel, a dust detection air channel and a double-photoacoustic spectrometry detection mechanism which are mutually connected in parallel.

The NOx detection air channel includes a front air pipe, a background interference detection air pipe, a $NO_2$ detection air pipe and a NO detection air pipe that communicate with the front air pipe through a four-way control valve and are mutually connected in parallel, a rear air pipe communicating with the background interference detection air pipe, the $NO_2$ detection air pipe and the NO detection air pipe through a four-way pipe, and a NOx photoacoustic detection cavity communicating with the rear air pipe; and a filtering membrane is mounted on the front air pipe, a NOx activated carbon adsorbent is filled in the background interference detection air pipe, and a mercury lamp is mounted on the NO detection air pipe.

The dust detection air channel includes a dust detection air pipe and a dust photoacoustic detection cavity communicating with the dust detection air pipe.

The double-photoacoustic spectrometry detection mechanism includes a laser device configured to emit laser to the NOx photoacoustic detection cavity and the dust photoacoustic detection cavity, a signal modulator connected with the laser device, a lock-in amplifier connected with the signal modulator, a computer connected with the lock-in amplifier, a rheomicrophone I mounted on the NOx photoacoustic detection cavity and connected with the lock-in amplifier, and a rheomicrophone II mounted on the dust photoacoustic detection cavity and connected with the lock-in amplifier.

Further, the NOx photoacoustic detection cavity and the dust photoacoustic detection cavity are arranged side by side, the laser device aligns with the NOx photoacoustic detection cavity, the double-photoacoustic spectrometry detection mechanism further includes two reflecting mirrors separately arranged on rear sides of the NOx photoacoustic detection cavity and the dust photoacoustic detection cavity, and the laser, emitted from the NOx photoacoustic detection cavity, may irradiate into the dust photoacoustic detection cavity through the two reflecting mirrors.

Further, front ends of the NOx detection air channel and the dust detection air channel are connected with an air inlet pipe through a three-way pipe while rear ends of the NOx detection air channel and the dust detection air channel are connected with an air outlet pipe through the three-way pipe, and a sampling pump is mounted on the air outlet pipe.

The present disclosure further provides a detection method for a gas mass content by applying the foregoing synchronous detection system for the trace nitrogen-oxygen compound based on the photoacoustic spectrometry, including the following steps of: synchronously inputting to-be-tested gas to a NOx detection air channel and a dust detection air channel, starting a double-photoacoustic spectrometry detection mechanism, where the to-be-tested gas entering the NOx detection air channel enters a NOx photoacoustic detection cavity through a background interference detection air pipe, a $NO_2$ detection air pipe and a NO detection air pipe in respective under the control of a four-way control valve, a local interference gas content $S_{background}$, a $NO_2$ gas content $S_{NO2}$ and a NO gas content $S_{NO}$ in the to-be-tested gas are separately obtained upon the detection of the double-photoacoustic spectrometry detection mechanism, and the to-be-tested gas entering the dust detection air channel enters the dust photoacoustic detection cavity and is subjected to the detection of the double-photoacoustic spectrometry detection mechanism, to obtain a dust content $S_{dust}$ in the to-be-tested gas.

Further, a rear end of the ONx detection air channel is provided with a flowmeter I configured to control a gas flow of the NOx photoacoustic detection cavity, a rear end of the dust detection air channel is provided with a flowmeter II configured to control a gas flow of the dust photoacoustic detection cavity, and the NO detection air pipe is provided with a flowmeter III configured to control a gas flow that flows through the mercury lamp and participates in a reaction.

Further, a detection process for $S_{background}$ in the to-be-tested gas includes the following steps of:

step 1: starting a sampling pump for air exhaust, dividing the to-be-tested gas into two air channels, one controlling the gas flow of the NOx photoacoustic detection cavity through the flowmeter I, and the other controlling the gas flow of the dust photoacoustic detection cavity through the flowmeter II;

step 2: regulating a four-way control valve such that the to-be-tested gas enters a background interference detection air pipe, that is, the to-be-tested gas entering the NOx photoacoustic detection cavity through a sampling pipe, a dust filtering membrane, the four-way control valve and a NOx activated carbon adsorbent sequentially, at this time the dust filtering membrane filtering and removing partial dust, the NOx activated carbon adsorbent filtering and removing NOx, and the remaining local interference gas entering the NOx photoacoustic detection cavity;

step 3: starting a laser device, through a signal modulator, the laser device emitting ultraviolet spectrum band laser that irradiates into the NOx photoacoustic detection cavity, and the laser exciting the local interference gas based on a photoacoustic effect to generate a sound pressure band and drive a rheomicrophone I to generate a photoacoustic signal $P_1$; and step 4: the photoacoustic signal $P_1$ being in direct proportion to the local interference gas content $S_{background}$, and after being collected and amplified by a detection lock-in amplifier that is modulated by the same signal modulator, the photoacoustic signal $P_1$ being processed on a computer to obtain and display the local interference gas content $S_{background}$.

Further, a detection process for $S_{NO2}$ in the to-be-tested gas includes the following steps of:

step 1: starting a sampling pump for air exhaust, dividing the to-be-tested gas into two air channels, one controlling the gas flow of the NOx photoacoustic detection cavity through the flowmeter I, and the other controlling the gas flow of the dust photoacoustic detection cavity through the flowmeter II;

step 2: regulating a four-way control valve such that the to-be-tested gas enters a $NO_2$ detection air pipe, that is, the to-be-tested gas entering the NOx photoacoustic detection cavity through a sampling pipe, a dust filtering membrane, the four-way control valve and the $NO_2$ detection air pipe sequentially, at this time the dust filtering membrane filtering and removing partial dust, and the remaining local interference gas and $NO_2$ entering the NOx photoacoustic detection cavity;

step 3: starting a laser device, through a signal modulator, the laser device emitting ultraviolet spectrum band laser that irradiates into the NOx photoacoustic detection cavity, and the laser exciting the local interference gas and $NO_2$ based on a photoacoustic effect to generate a sound pressure band and drive a rheomicrophone I to generate a photoacoustic signal $P_2$, and $P_2$ subtracting the photoacoustic signal $P_1$ excited by the local interference gas to obtain a photoacoustic signal $P_3$ execited by the $NO_2$ gas; and step 4: the photoacoustic signal $P_3$ being in direct proportion to the total content $S_{NO2}$ of $NO_2$, and after being collected and amplified by a detection lock-in amplifier that is modulated by the same signal modulator, the photoacoustic signal $P_3$ being processed on a computer to obtain and display the content $S_{NO2}$ of the $NO_2$ gas.

Further, a detection process for $S_{NO}$ in the to-be-tested gas includes the following steps of:

step 1: starting a sampling pump for air exhaust, dividing the to-be-tested gas into two air channels, one controlling the gas flow of the NOx photoacoustic detection cavity through the flowmeter I, and the other controlling the gas flow of the dust photoacoustic detection cavity through the flowmeter II;

step 2: regulating a four-way control valve such that the to-be-tested gas enters a NO detection air pipe, that is, the to-be-tested gas entering the NOx photoacoustic detection cavity through a sampling pipe, a dust filtering membrane, the four-way control valve and a mercury lamp sequentially, at this time the dust filtering membrane filtering and removing partial dust, the mercury lamp being powered on to generate excess ozone, reacting with NO to generate $NO_2$, and the to-be-tested gas entering the NOx photoacoustic detection cavity being the local interference gas, the $NO_2$ generated from the reaction and the original existing $NO_2$;

step 3: starting a laser device, through a signal modulator, the laser device emitting ultraviolet spectrum band laser that irradiates into the NOx photoacoustic detection cavity, and the laser exciting the local interference gas and $NO_2$ based on a photoacoustic effect to generate a sound pressure band and drive a rheomicrophone I to generate a photoacoustic signal $P_4$, and $P_4$ subtracting the original existing photoacoustic signals $P_1$ and $P_2$ excited by the local interference gas and the $NO_2$ gas to obtain a photoacoustic signal $P_5$ excited by the $NO_2$ gas; and step 4: the photoacoustic signal $P_5$ being in direct proportion to the total content $S_{NO}$ of NO, and after being collected and amplified by a detection lock-in amplifier that is modulated by the same signal modulator, the photoacoustic signal $P_5$ being processed on a computer to obtain and display the content $S_{NO}$ of the NO gas.

Further, a detection process for $S_{dust}$ in the to-be-tested gas includes the following steps of:

step 1: starting a sampling pump for air exhaust, dividing the to-be-tested gas into two air channels, one controlling the gas flow of the NOx photoacoustic detection cavity through the flowmeter I, and the other controlling the gas flow of the dust photoacoustic detection cavity through the flowmeter II;

step 2: starting a laser device, through a signal modulator, the laser device emitting ultraviolet spectrum band laser that irradiates into the dust photoacoustic detection cavity, and the laser exciting the local interference gas, $NO_2$ and dust based on a photoacoustic effect to generate a sound pressure band and drive a rheomicrophone II to generate a photoacoustic signal $P_6$, and $P_6$ subtracting the original existing photoacoustic signals $P_1$ and $P_2$ excited by the local interference gas and the $NO_2$ gas to obtain a photoacoustic signal $P_7$ excited by gaseous dust; and step 3: the photoacoustic signal $P_7$ being in direct proportion to the dust content $S_{dust}$, and after being collected and amplified by a detection lock-in amplifier that is modulated by the same signal modulator, the photoacoustic signal $P_7$ being processed on a computer to obtain and display the dust content $S_{dust}$.

The beneficial effects of the present disclosure are reflected as follows.

In the present disclosure, the laser device outputs a square wave modulating signal through the signal modulator and emits the ultraviolet spectrum specific band laser (405 nm) that irradiates into the NOx photoacoustic detection cavity; according to an absorption and response cross section, the laser in this band may excite the local interference gas and $NO_2$ based on the photoacoustic effect to generate the sound pressure band and drive the rheomicrophone to generate the photoacoustic signal, however the substance content is in direct proportion to the photoacoustic signal, so the content of the local interference gas and $NO_2$ can be obtained through backward inference, then the mercury lamp emits the excess $O_3$ that reacts with NO to generate $NO_2$, the content of $NO_2$ is detected through differential detection, and the NO content is deduced, thus solving the puzzle that the ultraviolet band is hard to detect NO; and the setting of the double-photoacoustic spectrometry system is of great significance to provide NO and $NO_2$ with dust detection data in real time and to analyze the pollution mechanism thereof, and the air channel switching detection for NO and $NO_2$ is of great significance to obtain two gas supply methods synchronously and to research the chemical reaction property of the nitrogen-oxygen compound.

BRIEF DESCRIPTION OF THE DRAWINGS

FIG. 1 is a structural diagram of a synchronous detection system for a trace nitrogen-oxygen compound based on photoacoustic spectrometry in one embodiment of the present disclosure.

DETAILED DESCRIPTION OF THE EMBODIMENTS

The following clearly and completely describes the technical solutions in the embodiments of the present disclosure in conjunction with the accompanying drawings in the embodiments of the present disclosure. Apparently, the described embodiments are some rather than all of the embodiments of the present disclosure. The embodiments in this application and features in the embodiments may be combined with each other without conflict. Based on the embodiments of the present disclosure, all the other embodiments obtained by those of ordinary skill in the art on the premise of not contributing creative effort should belong to the protection scope of the present disclosure.

It is to be noted that if directional indication, such as: upper, lower, left, right, front, rear, etc. is involved in the embodiments of the present disclosure, the directional indication is merely used to explain the relative position relation, movement and the like of various components under a certain special posture (as shown in the drawings); and if the special posture is changed, the directional indication will change accordingly.

In addition, if the descriptions "first", "second" and the like are involved in the embodiments of the present disclosure, the descriptions "first", "second" and the like are merely used for description, instead of being understood as indicating or implying relative importance or impliedly indicating the quantity of the showed technical features. Thus, the features defined with "first" and "second" may expressly or impliedly one or more features. In addition, the meaning of "and/or" in the text includes three parallel schemes, take "A and/or B" for example, including A scheme, or B scheme, or the scheme meeting A and B at the same time. In addition, "a plurality of" means two or above two. Thus, the technical solutions of various embodiments may be mutually combined, but must be achieved by those of ordinary skill in the art. When the combination of the technical solution has mutual contradiction or cannot be achieved, it should believe that such combination of the technical solution does not exist.

Referring to FIG. 1, a synchronous detection system for a trace nitrogen-oxygen compound based on photoacoustic spectrometry provided by the present disclosure includes a NOx detection air channel, a dust detection air channel and a double-photoacoustic spectrometry detection mechanism which are mutually connected in parallel.

The NOx detection air channel includes a front air pipe 101, a background interference detection air pipe 103, a $NO_2$ detection air pipe 104 and a NO detection air pipe 105 that communicate with the front air pipe 101 through a four-way control valve 102 and are mutually connected in parallel, a rear air pipe 107 communicating with the background interference detection air pipe 103, the $NO_2$ detection air pipe 104 and the NO detection air pipe 105 through a four-way pipe 106, and a NOx photoacoustic detection cavity 108 communicating with the rear air pipe 107; and a filtering membrane 109 is mounted on the front air pipe 101, a NOx activated carbon adsorbent 110 is filled in the background interference detection air pipe 103, and a mercury lamp 111 is mounted on the NO detection air pipe 105.

The dust detection air channel includes a dust detection air pipe 201 and a dust photoacoustic detection cavity 202 communicating with the dust detection air pipe 201.

The double-photoacoustic spectrometry detection mechanism includes a laser device 301 configured to emit laser to the NOx photoacoustic detection cavity 108 and the dust photoacoustic detection cavity 202, a signal modulator 302 connected with the laser device 301, a lock-in amplifier 303 connected with the signal modulator 302, a computer 304 connected with the lock-in amplifier 303, a rheomicrophone I 305 mounted on the NOx photoacoustic detection cavity 108 and connected with the lock-in amplifier 303, and a rheomicrophone II 306 mounted on the dust photoacoustic detection cavity 202 and connected with the lock-in amplifier 303.

In one embodiment, the NOx photoacoustic detection cavity 108 and the dust photoacoustic detection cavity 202 are arranged side by side, the laser device 301 aligns with the NOx photoacoustic detection cavity 108, the double-photoacoustic spectrometry detection mechanism further includes two reflecting mirrors 307 separately arranged on rear sides of the NOx photoacoustic detection cavity 108 and the dust photoacoustic detection cavity 202, and the laser, emitted from the NOx photoacoustic detection cavity 108, may irradiate into the dust photoacoustic detection cavity 202 through the two reflecting mirrors 307. Only one laser device is required to implement the emission of the laser into the NOx photoacoustic detection cavity and the dust photoacoustic detection cavity synchronously through this design, which not only has a simple structure and a convenient operation, but also has high synchronization.

In one embodiment, both the NOx photoacoustic detection cavity 108 and the dust photoacoustic detection cavity 202 are in cylindrical design, and both ends are mounted with quartz windows through rubber seal rings. This design facilitates the excitation of corresponding substances by the laser, and the quartz windows on both ends are used for transmitting the laser.

In one embodiment, the rheomicrophone I 305 and the rheomicrophone II 306 are plugged at middles of the NOx photoacoustic detection cavity 108 and the dust photoacoustic detection cavity 202, and sealed by the rubber seal rings. This design enables the rheomicrophone to collect the sound pressure band more easily, with a better testing effect.

During specific implementation, an amplifier for amplifying the signal of the rheomicrophone is also provided, and after being amplified, the signal of the rheomicrophone is collected again by the lock-in amplifier.

In one embodiment, front ends of the NOx detection air channel and the dust detection air channel are connected with an air inlet pipe 308 through a three-way pipe while rear ends of the NOx detection air channel and the dust detection air channel are connected with an air outlet pipe 309 through the three-way pipe, and a sampling pump 310 is mounted on the air outlet pipe 309. Through this design, the sampling pump is started, facilitating the synchronous air inlet of the two detection air channels.

In the present disclosure, the laser device outputs a square wave modulating signal through the signal modulator and emits the ultraviolet spectrum specific band laser (405 nm) that irradiates into the NOx photoacoustic detection cavity; according to an absorption and response cross section, the laser in this band may excite the local interference gas and $NO_2$ based on the photoacoustic effect to generate the sound pressure band and drive the rheomicrophone to generate the photoacoustic signal, however the substance content is in direct proportion to the photoacoustic signal, so the content of the local interference gas and $NO_2$ can be obtained through backward inference, then the mercury lamp emits the excess $O_3$ that reacts with NO to generate $NO_2$, the content of $NO_2$ is detected through differential detection, and the NO content is deduced, thus solving the puzzle that the ultraviolet band is hard to detect NO; and the setting of the double-photoacoustic spectrometry system is of great significance to provide NO and $NO_2$ with dust detection data in real time and to analyze the pollution mechanism thereof, and the air channel switching detection for NO and $NO_2$ is of great significance to obtain two gas supply methods synchronously and to research the chemical reaction property of the nitrogen-oxygen compound.

A detection method for a gas mass content by applying the foregoing synchronous detection system for the trace nitrogen-oxygen compound based on the photoacoustic spectrometry provided by the present disclosure, including the following steps of: synchronously inputting to-be-tested gas to a NOx detection air channel and a dust detection air channel, starting a double-photoacoustic spectrometry detection mechanism, where the to-be-tested gas entering the NOx detection air channel enters a NOx photoacoustic detection cavity 108 through a background interference detection air pipe 103, a $NO_2$ detection air pipe 104 and a NO detection air pipe 105 in respective under the control of a four-way control valve 102, a local interference gas content $S_{background}$, a $NO_2$ gas content $S_{NO2}$ and a NO gas content $S_{NO}$ in the to-be-tested gas are separately obtained upon the detection of the double-photoacoustic spectrometry detection mechanism, and the to-be-tested gas entering the dust detection air channel enters the dust photoacoustic detection cavity 202 and is subjected to the detection of the double-photoacoustic spectrometry detection mechanism, to obtain a dust content $S_{dust}$ in the to-be-tested gas.

In one embodiment, a rear end of the ONx detection air channel is provided with a flowmeter I 112 configured to control a gas flow of the NOx photoacoustic detection cavity 108, a rear end of the dust detection air channel is provided with a flowmeter II 203 configured to control a gas flow of the dust photoacoustic detection cavity 202, and the NO detection air pipe 105 is provided with a flowmeter III 113 configured to control a gas flow that flows through the mercury lamp 111 and participates in a reaction.

Specifically, a detection process for $S_{background}$ in the to-be-tested gas includes the following steps of:
step 1: starting a sampling pump 310 for air exhaust, dividing the to-be-tested gas into two air channels, one controlling the gas flow of the NOx photoacoustic detection cavity 108 through the flowmeter I 112, and the other controlling the gas flow of the dust photoacoustic detection cavity 202 through the flowmeter II 203;

step 2: regulating a four-way control valve 102 such that the to-be-tested gas enters a background interference detection air pipe 103, that is, the to-be-tested gas entering the NOx photoacoustic detection cavity 108 through a sampling pipe, a dust filtering membrane, the four-way control valve 102 and a NOx activated carbon adsorbent 110 sequentially, at this time the dust filtering membrane filtering and removing partial dust, the NOx activated carbon adsorbent 110 filtering and removing NOx, and the remaining local interference gas entering the NOx photoacoustic detection cavity 108;

step 3: starting a laser device 301, through a signal modulator 302, the laser device 301 emitting ultraviolet spectrum band laser that irradiates into the NOx photoacoustic detection cavity 108, and the laser exciting the local interference gas based on a photoacoustic effect to generate a sound pressure band and drive a rheomicrophone I 305 to generate a photoacoustic signal $P_1$; and step 4: the photoacoustic signal $P_1$ being in direct proportion to the local interference gas content $S_{background}$, and after being collected and amplified by a detection lock-in amplifier 303 that is modulated by the same signal modulator 302, the photoacoustic signal $P_1$ being processed on a computer 304 to obtain and display the local interference gas content $S_{background}$.

A detection process for $S_{NO2}$ in the to-be-tested gas includes the following steps of:
step 1: starting a sampling pump 310 for air exhaust, dividing the to-be-tested gas into two air channels, one controlling the gas flow of the NOx photoacoustic detection cavity 108 through the flowmeter I 112, and the other controlling the gas flow of the dust photoacoustic detection cavity 202 through the flowmeter II 203;

step 2: regulating a four-way control valve 102 such that the to-be-tested gas enters a $NO_2$ detection air pipe 104, that is, the to-be-tested gas sequentially entering the NOx photoacoustic detection cavity 108 through a sampling pipe, a dust filtering membrane, the four-way control valve 102 and the $NO_2$ detection air pipe 104, at this time the dust filtering membrane filtering and removing partial dust, and the remaining local interference gas and $NO_2$ entering the NOx photoacoustic detection cavity 108;

step 3: starting a laser device 301, through a signal modulator 302, the laser device 301 emitting ultraviolet spectrum band laser that irradiates into the NOx photoacoustic detection cavity 108, and the laser exciting the local interference gas and $NO_2$ based on a photoacoustic effect to generate a sound pressure band and drive a rheomicrophone I 305 to generate a photoacoustic signal $P_2$, and $P_2$ subtracting the photoacoustic signal $P_1$ excited by the local interference gas to obtain a photoacoustic signal $P_3$ excited by the $NO_2$ gas; and step 4: the photoacoustic signal $P_3$ being in direct proportion to the total content $S_{NO2}$ of $NO_2$, and after being collected and amplified by a detection lock-in amplifier 303 that is modulated by the same signal modulator 302, the photoacoustic signal $P_3$ being processed on a computer 304 to obtain and display the content $S_{NO2}$ of the $NO_2$ gas.

A detection process for $S_{NO}$ in the to-be-tested gas includes the following steps of:

step 1: starting a sampling pump 310 for air exhaust, dividing the to-be-tested gas into two air channels, one controlling the gas flow of the NOx photoacoustic detection cavity 108 through the flowmeter I 112, and the other controlling the gas flow of the dust photoacoustic detection cavity 202 through the flowmeter II 203;

step 2: regulating a four-way control valve 102 such that the to-be-tested gas enters a NO detection air pipe 105, that is, the to-be-tested gas entering the NOx photoacoustic detection cavity 108 through a sampling pipe, a dust filtering membrane, the four-way control valve 102 and a mercury lamp 111 sequentially, at this time the dust filtering membrane filtering and removing partial dust, the mercury lamp 111 being powered on to generate excess ozone, reacting with NO to generate $NO_2$, and the to-be-tested gas entering the NOx photoacoustic detection cavity 108 being the local interference gas, the $NO_2$ generated from the reaction and the original existing $NO_2$;

step 3: starting a laser device 301, through a signal modulator 302, the laser device 301 emitting ultraviolet spectrum band laser that irradiates into the NOx photoacoustic detection cavity 108, and the laser exciting the local interference gas and $NO_2$ based on a photoacoustic effect to generate a sound pressure band and drive a rheomicrophone I 305 to generate a photoacoustic signal $P_4$, and $P_4$ subtracting the original existing photoacoustic signals $P_1$ and $P_2$ excited by the local interference gas and the $NO_2$ gas to obtain a photoacoustic signal $P_5$ excited by the $NO_2$ gas; and step 4: the photoacoustic signal $P_5$ being in direct proportion to the total content $S_{NO}$ of NO, and after being collected and amplified by a detection lock-in amplifier 303 that is modulated by the same signal modulator 302, the photoacoustic signal $P_5$ being processed on a computer 304 to obtain and display the content $S_{NO}$ of the NO gas.

A detection process for $S_{dust}$ in the to-be-tested gas includes the following steps of:

step 1: starting a sampling pump 310 for air exhaust, dividing the to-be-tested gas into two air channels, one controlling the gas flow of the NOx photoacoustic detection cavity 108 through the flowmeter I 112, and the other controlling the gas flow of the dust photoacoustic detection cavity 202 through the flowmeter II 203;

step 2: starting a laser device 301, through a signal modulator 302, the laser device 301 emitting ultraviolet spectrum band laser that irradiates into the dust photoacoustic detection cavity 202, and the laser exciting the local interference gas, $NO_2$ and dust based on a photoacoustic effect to generate a sound pressure band and drive a rheomicrophone II 306 to generate a photoacoustic signal $P_6$, and $P_6$ subtracting the original existing photoacoustic signals $P_1$ and $P_2$ excited by the local interference gas and the $NO_2$ gas to obtain a photoacoustic signal $P_7$ excited by gaseous dust; and step 3: the photoacoustic signal $P_7$ being in direct proportion to the dust content $S_{dust}$, and after being collected and amplified by a detection lock-in amplifier 303 that is modulated by the same signal modulator 302, the photoacoustic signal $P_7$ being processed on a computer 304 to obtain and display the dust content $S_{dust}$.

The above are only optional embodiments of the present disclosure and not intended to limit the present disclosure. Any modifications, equivalent replacements, improvements and the like made within the spirit and principle of the present disclosure shall fall within the protection scope of the present disclosure.

What is claimed is:

1. A synchronous detection system for a trace nitrogen-oxygen compound based on photoacoustic spectrometry, comprising a NOx (Nitrogen Oxide) detection air channel, a dust detection air channel and a double-photoacoustic spectrometry detection mechanism which are mutually connected in parallel; wherein:

the NOx detection air channel comprises a front air pipe, a background interference detection air pipe, a $NO_2$ detection air pipe and a NO detection air pipe that communicate with the front air pipe through a four-way control valve and are mutually connected in parallel, a rear air pipe communicating with the background interference detection air pipe, the $NO_2$ detection air pipe and the NO detection air pipe through a four-way pipe, and a NOx photoacoustic detection cavity communicating with the rear air pipe; and a filtering membrane is mounted on the front air pipe, a NOx activated carbon adsorbent is filled in the background interference detection air pipe, and a mercury lamp is mounted on the NO detection air pipe;

the dust detection air channel comprises a dust detection air pipe and a dust photoacoustic detection cavity communicating with the dust detection air pipe;

the double-photoacoustic spectrometry detection mechanism comprises a laser device configured to emit laser to the NOx photoacoustic detection cavity and the dust photoacoustic detection cavity, a signal modulator connected with the laser device, a lock-in amplifier connected with the signal modulator, a computer connected with the lock-in amplifier, a rheomicrophone I mounted on the NOx photoacoustic detection cavity and connected with the lock-in amplifier, and a rheomicrophone II mounted on the dust photoacoustic detection cavity and connected with the lock-in amplifier;

the NOx photoacoustic detection cavity and the dust photoacoustic detection cavity are arranged side by side, the laser device aligns with the NOx photoacoustic detection cavity, the double-photoacoustic spectrometry detection mechanism further comprises two reflecting mirrors separately arranged on rear sides of the NOx photoacoustic detection cavity and the dust photoacoustic detection cavity, and the laser, emitted from the NOx photoacoustic detection cavity, irradiates into the dust photoacoustic detection cavity through the two reflecting mirrors;

front ends of the NOx detection air channel and the dust detection air channel are connected with an air inlet pipe through a three-way pipe while rear ends of the NOx detection air channel and the dust detection air channel are connected with an air outlet pipe through the three-way pipe, and a sampling pump is mounted on the air outlet pipe;

a detection method for a gas mass content by the synchronous detection system for the trace nitrogen-oxygen compound based on the photoacoustic spectrometry comprises the following steps of:

synchronously inputting to-be-tested gas to the NOx detection air channel and the dust detection air channel;

starting the double-photoacoustic spectrometry detection mechanism, wherein:

the to-be-tested gas entering the NOx detection air channel enters the NOx photoacoustic detection cavity through the background interference detection air pipe, the $NO_2$ detection air pipe and the NO detection air pipe in respective under the control of the four-way control valve, a local interference gas content $S_{background}$, a $NO_2$ gas content $S_{NO2}$ and a NO gas content $S_{NO}$ in the to-be-tested gas are separately obtained upon a detection of the double-photoacoustic spectrometry detection mechanism, and the to-be-tested gas entering the dust detection air channel enters the dust photoacoustic detection cavity and is subjected to the detection of the double-photoacoustic spectrometry detection mechanism, to obtain a dust content $S_{dust}$ in the to-be-tested gas; and a rear end of the NOx detection air channel is provided with a flowmeter I configured to control a gas flow of the NOx photoacoustic detection cavity, a rear end of the dust detection air channel is provided with a flowmeter II configured to control a gas flow of the dust photoacoustic detection cavity, and the NO detection air pipe is provided with a flowmeter III configured to control a gas flow that flows through the mercury lamp and participates in a reaction.

2. The synchronous detection system for the trace nitrogen-oxygen compound based on the photoacoustic spectrometry according to claim 1, wherein a detection process for $S_{background}$ in the to-be-tested gas comprises the following steps of:

step 1: starting the sampling pump for air exhaust, dividing the to-be-tested gas into two air channels, one controlling the gas flow of the NOx photoacoustic detection cavity through the flowmeter I, and the other controlling the gas flow of the dust photoacoustic detection cavity through the flowmeter II;

step 2: regulating the four-way control valve such that the to-be-tested gas enters the background interference detection air pipe, that is, the to-be-tested gas entering the NOx photoacoustic detection cavity through a sampling pipe, a dust filtering membrane, the four-way control valve and the NOx activated carbon adsorbent sequentially, at this time the dust filtering membrane filtering and removing partial dust, the NOx activated carbon adsorbent filtering and removing NOx, and the remaining local interference gas entering the NOx photoacoustic detection cavity;

step 3: starting the laser device, through the signal modulator, the laser device emitting ultraviolet spectrum band laser that irradiates into the NOx photoacoustic detection cavity, and the laser exciting the local interference gas based on a photoacoustic effect to generate a sound pressure band and drive the rheomicrophone I to generate a photoacoustic signal $P_1$; and step 4: the photoacoustic signal $P_1$ being in direct proportion to the local interference gas content $S_{background}$, and after being collected and amplified by a detection lock-in amplifier that is modulated by a same signal modulator, the photoacoustic signal $P_1$ being processed on the computer to obtain and display the local interference gas content $S_{background}$.

3. The synchronous detection system for the trace nitrogen-oxygen compound based on the photoacoustic spectrometry according to claim 2, wherein a detection process for $S_{NO2}$ in the to-be-tested gas comprises the following steps of:

step 1: starting the sampling pump for air exhaust, dividing the to-be-tested gas into two air channels, one controlling the gas flow of the NOx photoacoustic detection cavity through the flowmeter I, and the other controlling the gas flow of the dust photoacoustic detection cavity through the flowmeter II;

step 2: regulating the four-way control valve such that the to-be-tested gas enters the $NO_2$ detection air pipe, that is, the to-be-tested gas entering the NOx photoacoustic detection cavity through the sampling pipe, the dust filtering membrane, the four-way control valve and the $NO_2$ detection air pipe sequentially, at this time the dust filtering membrane filtering and removing partial dust, and the remaining local interference gas and $NO_2$ entering the NOx photoacoustic detection cavity;

step 3: starting the laser device, through the signal modulator, the laser device emitting ultraviolet spectrum band laser that irradiates into the NOx photoacoustic detection cavity, and the laser exciting the local interference gas and $NO_2$ based on the photoacoustic effect to generate the sound pressure band and drive the rheomicrophone I to generate a photoacoustic signal $P_2$, and $P_2$ subtracting the photoacoustic signal $P_1$ excited by the local interference gas to obtain a photoacoustic signal $P_3$ excited by the $NO_2$ gas; and step 4: the photoacoustic signal $P_3$ being in direct proportion to the total content $S_{NO2}$ of $NO_2$, and after being collected and amplified by the detection lock-in amplifier that is modulated by the same signal modulator, the photoacoustic signal $P_3$ being processed on the computer to obtain and display the content $S_{NO2}$ of the $NO_2$ gas.

4. The synchronous detection system for the trace nitrogen-oxygen compound based on the photoacoustic spectrometry according to claim 2, wherein a detection process for $S_{NO}$ in the to-be-tested gas comprises the following steps of:

step 1: starting the sampling pump for air exhaust, dividing the to-be-tested gas into two air channels, one controlling the gas flow of the NOx photoacoustic detection cavity through the flowmeter I, and the other controlling the gas flow of the dust photoacoustic detection cavity through the flowmeter II;

step 2: regulating the four-way control valve such that the to-be-tested gas enters the NO detection air pipe, that is, the to-be-tested gas entering the NOx photoacoustic detection cavity through the sampling pipe, the dust filtering membrane, the four-way control valve and the mercury lamp sequentially, at this time the dust filtering membrane filtering and removing partial dust, the mercury lamp being powered on to generate excess ozone, reacting with NO to generate $NO_2$, and the to-be-tested gas entering the NOx photoacoustic detection cavity being the local interference gas, the $NO_2$ generated from the reaction and an original existing $NO_2$;

step 3: starting the laser device, through the signal modulator, the laser device emitting ultraviolet spectrum band laser that irradiates into the NOx photoacoustic detection cavity, and the laser exciting the local interference gas and $NO_2$ based on the photoacoustic effect to generate the sound pressure band and drive the rheomicrophone I to generate a photoacoustic signal $P_4$, and $P_4$ subtracting original existing photoacoustic signals $P_1$ and $P_2$ excited by the local interference gas and the $NO_2$ gas to obtain a photoacoustic signal $P_5$ excited by the $NO_2$ gas; and step 4: the photoacoustic signal $P_5$ being in direct proportion to the total content $S_{NO}$ of NO, and after being collected and amplified by the detection lock-in amplifier that is modulated by the same signal modulator, the photoacoustic signal $P_5$ being processed on the computer to obtain and display the content $S_{NO}$ of the NO gas.

5. The synchronous detection system for the trace nitrogen-oxygen compound based on the photoacoustic spectrometry according to claim 2, wherein a detection process for $S_{dust}$ in the to-be-tested gas comprises the following steps of:

step 1: starting the sampling pump for air exhaust, dividing the to-be-tested gas into two air channels, one controlling the gas flow of the NOx photoacoustic detection cavity through the flowmeter I, and the other controlling the gas flow of the dust photoacoustic detection cavity through the flowmeter II;

step 2: starting the laser device, through the signal modulator, the laser device emitting ultraviolet spectrum band laser that irradiates into the dust photoacoustic detection cavity, and the laser exciting the local interference gas, $NO_2$ and dust based on the photoacoustic effect to generate the sound pressure band and drive the rheomicrophone II to generate a photoacoustic signal $P_6$, and $P_6$ subtracting original existing photoacoustic signals $P_1$ and $P_2$ excited by the local interference gas and the $NO_2$ gas to obtain a photoacoustic signal $P_7$ excited by gaseous dust; and step 3: the photoacoustic signal $P_7$ being in direct proportion to the dust content $S_{dust}$, and after being collected and amplified by the detection lock-in amplifier that is modulated by the same signal modulator, the photoacoustic signal $P_7$ being processed on the computer to obtain and display the dust content $S_{dust}$.

* * * * *